US012766309B2

(12) United States Patent
Farago et al.

(10) Patent No.: US 12,766,309 B2
(45) **Date of Patent: *Oct. 20, 2026**

(54) BLOOD PUMP SHAFT BEARING

(71) Applicant: Boston Scientific Scimed, Inc., Maple Grove, MN (US)

(72) Inventors: Laszlo T. Farago, Hudson, WI (US); Daniel H. VanCamp, Elk River, MN (US); Benjamin Breidall, Maple Grove, MN (US); Joseph A. Kronstedt, New Hope, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 19/171,672

(22) Filed: Apr. 7, 2025

(65) Prior Publication Data

US 2025/0229078 A1 Jul. 17, 2025

Related U.S. Application Data

(63) Continuation of application No. 18/095,738, filed on Jan. 11, 2023, now Pat. No. 12,290,676, which is a (Continued)

(51) Int. Cl.
*A61M 60/824* (2021.01)
*A61M 60/216* (2021.01)
(Continued)

(52) U.S. Cl.
CPC ........ *A61M 60/824* (2021.01); *A61M 60/216* (2021.01); *A61M 60/422* (2021.01); *A61M 60/508* (2021.01); *A61M 60/818* (2021.01); *F04D 13/026* (2013.01); *F04D 29/0467* (2013.01); *F16C 17/08* (2013.01); *F16C 33/103* (2013.01); *F16C 33/1045* (2013.01); *F16C 2316/18* (2013.01)

(58) Field of Classification Search
CPC ............... A61M 60/818; A61M 60/824; F04D 29/0467; F04D 29/9413; F04D 29/047; F04D 13/026; F16C 33/103; F16C 2316/18; F16C 17/08; F16C 17/045; F16C 17/105; F16C 17/107; F16C 19/12
See application file for complete search history.

(56) References Cited

U.S. PATENT DOCUMENTS

| | | | | |
|---|---|---|---|---|
| 4,427,310 A * | 1/1984 | Middleton | F16C 17/08 | 403/143 |
| 6,186,665 B1 * | 2/2001 | Maher | A61M 60/104 | 417/423.12 |
| 2014/0275722 A1 * | 9/2014 | Zimmermann | F04D 1/00 | 600/16 |

* cited by examiner

*Primary Examiner* — Kenneth J Hansen
(74) *Attorney, Agent, or Firm* — Seager, Tufte & Wickhem LLP

(57) ABSTRACT

A blood pump includes an impeller; a drive shaft coupled to the impeller and configured to rotate with the impeller; a motor configured to drive the impeller; and a bearing assembly disposed adjacent the motor and configured to receive an end of the drive shaft. The bearing assembly includes a bearing, where the end of the drive shaft is at least partially rounded, and the where the bearing includes a concave depression defined in a first side of the bearing, where the depression is configured to receive the end of the drive shaft. The bearing assembly may include a lubricant chamber configured to hold a lubricant.

20 Claims, 8 Drawing Sheets

Related U.S. Application Data continuation of application No. 16/657,246, filed on Oct. 18, 2019, now Pat. No. 11,565,103.

(60) Provisional application No. 62/747,346, filed on Oct. 18, 2018.

(51) Int. Cl.

| | |
|---|---|
| ***A61M 60/422*** | (2021.01) |
| ***A61M 60/508*** | (2021.01) |
| ***A61M 60/818*** | (2021.01) |
| ***F04D 13/02*** | (2006.01) |
| ***F04D 29/046*** | (2006.01) |
| ***F16C 17/08*** | (2006.01) |
| ***F16C 33/10*** | (2006.01) |

BLOOD PUMP SHAFT BEARING

CROSS-REFERENCE TO RELATED APPLICATION

This application is a continuation of U.S. patent application Ser. No. 18/095,738, filed Jan. 11, 2023, which is a continuation of U.S. patent application Ser. No. 16/657,246, filed Oct. 18, 2019, now U.S. Pat. No. 11,565,103, which claims priority to U.S. Provisional Patent Application No. 62/747,346, filed Oct. 18, 2018, the disclosures of which are herein incorporated by reference in their entireties.

TECHNICAL FIELD

The present disclosure relates to percutaneous circulatory support devices. More specifically, the disclosure relates to bearings using in percutaneous circulatory support devices.

BACKGROUND

Percutaneous circulatory support devices such as blood pumps typically provide circulatory support for up to approximately three weeks of continuous use. Wear at bearing surfaces can limit the lifetime of the devices. Additionally, heat generation and mechanical interactions with the blood at the bearing surface can lead to hemolysis, which can further lead to health complications such as anemia, requiring blood transfusions.

SUMMARY

In an Example 1, a bearing assembly configured to retain an end of a drive shaft of a blood pump, the bearing assembly comprising: a bearing; and a lubricant chamber configured to hold a lubricant.

In an Example 2, the bearing assembly of Example 1, wherein the end of the drive shaft is at least partially rounded, and the bearing comprising a concave depression defined in a first side of the bearing, wherein the depression is configured to receive the end of the drive shaft.

In an Example 3, the bearing assembly of either of Examples 1 or 2, further comprising a cup washer having a base and peripheral wall extending away from the base, forming a cavity bounded by an inner surface of the peripheral wall and an inner surface of the base, wherein the bearing is configured to be at least partially disposed within the cavity.

In an Example 4, the bearing assembly of Example 3, the cup washer further comprising a shaft aperture defined in the base, extending from the outer surface of the base to the inner surface of the base, wherein the shaft aperture is configured to receive a portion of the drive shaft.

In an Example 5, the bearing assembly of either of Examples 3 or 4, wherein at least a portion of the lubricant chamber is defined between the inner surface of the peripheral wall of the cup washer, the inner surface of the base of the cup washer, and a first side of the bearing.

In an Example 6, the bearing assembly of Example 2, the lubricant chamber comprising at least one channel defined in a second side of the bearing, the at least one channel passing through the depression, wherein the at least one channel is configured to retain lubricant.

In an Example 7, a blood pump, comprising: an impeller; a drive shaft coupled to the impeller and configured to rotate with the impeller; a motor configured to drive the impeller; and a bearing assembly disposed adjacent the motor and configured to receive an end of the drive shaft, the bearing assembly comprising a bearing, wherein the end of the drive shaft is at least partially rounded, and the wherein the bearing includes a concave depression defined in a first side of the bearing, wherein the depression is configured to receive the end of the drive shaft.

In an Example 8, the blood pump of Example 7, the bearing assembly further comprising a lubricant chamber configured to hold a lubricant.

In an Example 9, the blood pump of Example 8, the bearing assembly further comprising a cup washer having a base and peripheral wall extending away from the base, forming a cavity bounded by an inner surface of the peripheral wall and an inner surface of the base, wherein the bearing is configured to be at least partially disposed within the cavity.

In an Example 10, the blood pump of Example 9, the cup washer further comprising a shaft aperture defined in the base, extending from the outer surface of the base to the inner surface of the base, wherein the shaft aperture is configured to receive a portion of the drive shaft.

In an Example 11, the blood pump of either of Examples 9 or 10, wherein at least a portion of the lubricant chamber is defined between the inner surface of the peripheral wall of the cup washer, the inner surface of the base of the cup washer, and a first side of the bearing.

In an Example 12, the blood pump of Example 8, wherein the lubricant chamber is at least partially defined within the bearing.

In an Example 13, the blood pump of Example 12, the lubricant chamber comprising at least one channel defined in a second side of the bearing, the at least one channel passing through the depression, wherein the at least one channel is configured to retain lubricant.

In an Example 14, the blood pump of Example 13, the at least one channel comprising two channels that intersect one another in the depression.

In an Example 15, the blood pump of Example 8, the bearing assembly comprising a cylindrical-shaped bearing at an intersection of the drive shaft and a stationary shaft mounting pin, wherein the drive shaft is configured to rotate with respect to the stationary shaft mounting pin, and wherein the lubricant chamber is defined between an inner surface of the bearing and an outer surface of the stationary shaft mounting pin.

In an Example 16, a bearing assembly configured to retain an end of a drive shaft of a blood pump, the bearing assembly comprising: a bearing; and a lubricant chamber configured to hold a lubricant.

In an Example 17, the bearing assembly of Example 16, wherein the end of the drive shaft is at least partially rounded, and the bearing comprising a concave depression defined in a first side of the bearing, wherein the depression is configured to receive the end of the drive shaft.

In an Example 18, the bearing assembly of Example 16, further comprising a cup washer having a base and peripheral wall extending away from the base, forming a cavity bounded by an inner surface of the peripheral wall and an inner surface of the base, wherein the bearing is configured to be at least partially disposed within the cavity.

In an Example 19, the bearing assembly of Example 18, the cup washer further comprising a shaft aperture defined in the base, extending from the outer surface of the base to the inner surface of the base, wherein the shaft aperture is configured to receive a portion of the drive shaft.

In an Example 20, the bearing assembly of Example 19, wherein at least a portion of the lubricant chamber is defined between the inner surface of the peripheral wall of the cup washer, the inner surface of the base of the cup washer, and a first side of the bearing.

In an Example 21, the bearing assembly of Example 16, wherein the lubricant chamber is at least partially defined within the bearing.

In an Example 22, the bearing assembly of Example 21, the lubricant chamber comprising at least one channel defined in a second side of the bearing, the at least one channel passing through the depression, wherein the at least one channel is configured to retain lubricant.

In an Example 23, a blood pump, comprising: an impeller; a drive shaft coupled to the impeller and configured to rotate with the impeller; a motor configured to drive the impeller; and a bearing assembly disposed adjacent the motor and configured to receive an end of the drive shaft, the bearing assembly comprising a bearing, wherein the end of the drive shaft is at least partially rounded, and the wherein the bearing includes a concave depression defined in a first side of the bearing, wherein the depression is configured to receive the end of the drive shaft.

In an Example 24, the blood pump of Example 22, the bearing assembly further comprising a lubricant chamber configured to hold a lubricant.

In an Example 25, the blood pump of Example 24, the bearing assembly further comprising a cup washer having a base and peripheral wall extending away from the base, forming a cavity bounded by an inner surface of the peripheral wall and an inner surface of the base, wherein the bearing is configured to be at least partially disposed within the cavity.

In an Example 26, the blood pump of Example 24, the cup washer further comprising a shaft aperture defined in the base of the cup washer, extending from the outer surface of the base to the inner surface of the base, wherein the shaft aperture is configured to receive a portion of the drive shaft.

In an Example 27, the blood pump of Example 24, wherein at least a portion of the lubricant chamber is defined between the inner surface of the peripheral wall of the cup washer, the inner surface of the base of the cup washer, and a first side of the bearing.

In an Example 28, the blood pump of Example 24, wherein the lubricant chamber is at least partially defined within the bearing.

In an Example 29, the blood pump of Example 28, the lubricant chamber comprising at least one channel defined in a second side of the bearing, the at least one channel passing through the depression, wherein the at least one channel is configured to retain lubricant.

In an Example 30, the blood pump of Example 29, the at least one channel comprising two channels that intersect one another in the depression.

In an Example 31, the blood pump of Example 24, the bearing assembly comprising a cylindrical-shaped bearing at an intersection of the drive shaft and a stationary shaft mounting pin, wherein the drive shaft is configured to rotate with respect to the stationary shaft mounting pin, and wherein the lubricant chamber is defined between an inner surface of the bearing and an outer surface of the stationary shaft mounting pin.

In an Example 32, the blood pump of Example 23, further comprising another bearing assembly configured to receive another end of the drive shaft.

In an Example 33, a blood pump, comprising: an impeller; a drive shaft coupled to the impeller and configured to rotate with the impeller; a motor configured to drive the impeller; and a bearing assembly disposed adjacent the motor and configured to receive an end of the drive shaft, the bearing assembly comprising a bearing and a lubricant chamber configured to hold a lubricant.

In an Example 34, the blood pump of Example 33, wherein the end of the drive shaft is at least partially rounded, and the wherein the bearing includes a concave depression defined in a first side of the bearing, wherein the depression is configured to receive the end of the drive shaft.

In an Example 35, the blood pump of Example 34, the lubricant chamber comprising at least one channel defined in a second side of the bearing, the at least one channel passing through the depression, wherein the at least one channel is configured to retain lubricant.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

Figure 1A:
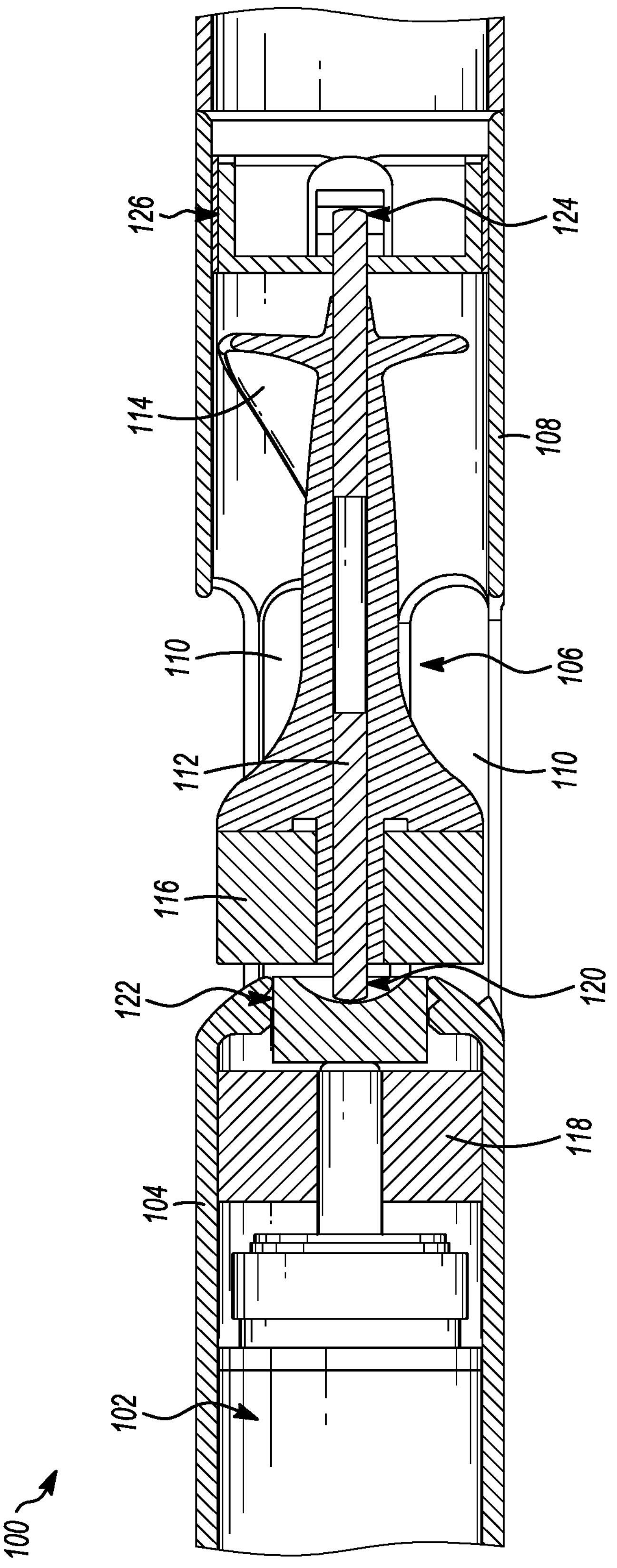
FIG. 1A depicts a cross-sectional side view of a portion of an illustrative percutaneous mechanical circulatory support device (also referred to herein, interchangeably, as a "blood pump"), in accordance with embodiments of the subject matter disclosed herein.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

As used herein in association with values (e.g., terms of magnitude, measurement, and/or other degrees of qualitative and/or quantitative observations that are used herein with respect to characteristics (e.g., dimensions, measurements, attributes, components, etc.) and/or ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a value, configuration, orientation, and/or other characteristic that is equal to (or the same as) the stated value, configuration, orientation, and/or other characteristic or equal to (or the same as) a value, configuration, orientation, and/or other characteristic that is reasonably close to the stated value, configuration, orientation, and/or other characteristic, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

The terms "up," "upper," and "upward," and variations thereof, are used throughout this disclosure for the sole purpose of clarity of description and are only intended to refer to a relative direction (i.e., a certain direction that is to be distinguished from another direction), and are not meant to be interpreted to mean an absolute direction. Similarly, the terms "down," "lower," and "downward," and variations thereof, are used throughout this disclosure for the sole purpose of clarity of description and are only intended to refer to a relative direction that is at least approximately opposite a direction referred to by one or more of the terms "up," "upper," and "upward," and variations thereof.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

DETAILED DESCRIPTION

Embodiments of the subject matter disclosed herein include bearing designs that may facilitate reducing heat formation by using lubrication, and reducing mechanical blood damage by preventing ingress of blood onto bearing surfaces. Bearing designs that include concave depressions and closed cavities facilitate preventing blood ingress onto bearing surfaces. Lubrication may be used to provide a fluid film at bearing surfaces to minimize wear. According to embodiments, any number of different types of lubricants may be used such as, for example, hydrophobic, water-insoluble lubricants (e.g., perfluoropolyether or poly-alpha-olefins classes of synthetic lubricants) may be used.

FIG. 1A depicts a cross-sectional side view of a portion of an illustrative percutaneous mechanical circulatory support device 100 (also referred to herein, interchangeably, as a "blood pump"), in accordance with embodiments of the subject matter disclosed herein. As shown in FIG. 1A, the circulatory support device 100 includes a motor 102 disposed within a motor housing 104. The motor 102 is configured to drive an impeller assembly 106 to provide a flow of blood through the device 100. The impeller assembly 106 is disposed within an impeller assembly housing 108, which includes a number of outlet apertures 110 defined therein. According to embodiments, the motor housing 104 and the impeller assembly housing 108 may be integrated with one another. In other embodiments, the motor housing 104 and the impeller assembly housing 108 may be separate components configured to be coupled together, either removeably or permanently.

A controller (not shown) is operably coupled to the motor 102 and is configured to control the motor 102. The controller may be disposed within the motor housing 104 in embodiments, or, in other embodiments, may be disposed outside the housing 104 (e.g., in a catheter handle, independent housing, etc.). In embodiments, the controller may include multiple components, one or more of which may be disposed within the housing 104. According to embodiments, the controller may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. Although the controller is referred to herein in the singular, the controller may be implemented in multiple instances, distributed across multiple computing devices, instantiated within multiple virtual machines, and/or the like.

As shown in FIG. 1A, the impeller assembly 106 includes a drive shaft 112 and an impeller 114 coupled thereto, where the drive shaft 112 is configured to rotate with the impeller 114. As shown, the drive shaft 112 is at least partially disposed within the impeller 114. In embodiments, the drive shaft 112 may be made of any number of different rigid materials such as, for example, steel, titanium alloys, cobalt chromium alloys, nitinol, high-strength ceramics, and/or the like. The impeller assembly 106 further includes an impeller rotor 116 coupled to, and at least partially surrounding, the drive shaft 112. The impeller rotor 116 may be any type of magnetic rotor capable of being driven by a stator 118 that is part of the motor 102. In this manner, as a magnetic field is applied to the impeller rotor 116 by the stator 118 in the motor 102, the rotor 116 rotates, causing the drive shaft 112 and impeller 114 to rotate.

As shown, the impeller assembly is maintained in its orientation by the drive shaft 112, which is retained, at a first end 120, by a first bearing assembly 122 and, at a second end 124, by a second bearing assembly 126. According to embodiments, the first bearing assembly 122 and the second bearing assembly 126 may include different types of bearings. According to embodiments, the first bearing assembly 122 and/or the second bearing assembly 126 may include lubrication, while, in other embodiments, one and/or the other may not include lubrication. Various embodiments of bearing technology are described herein with respect to the first and second bearing assemblies 122 and 126.

Figure 1B:
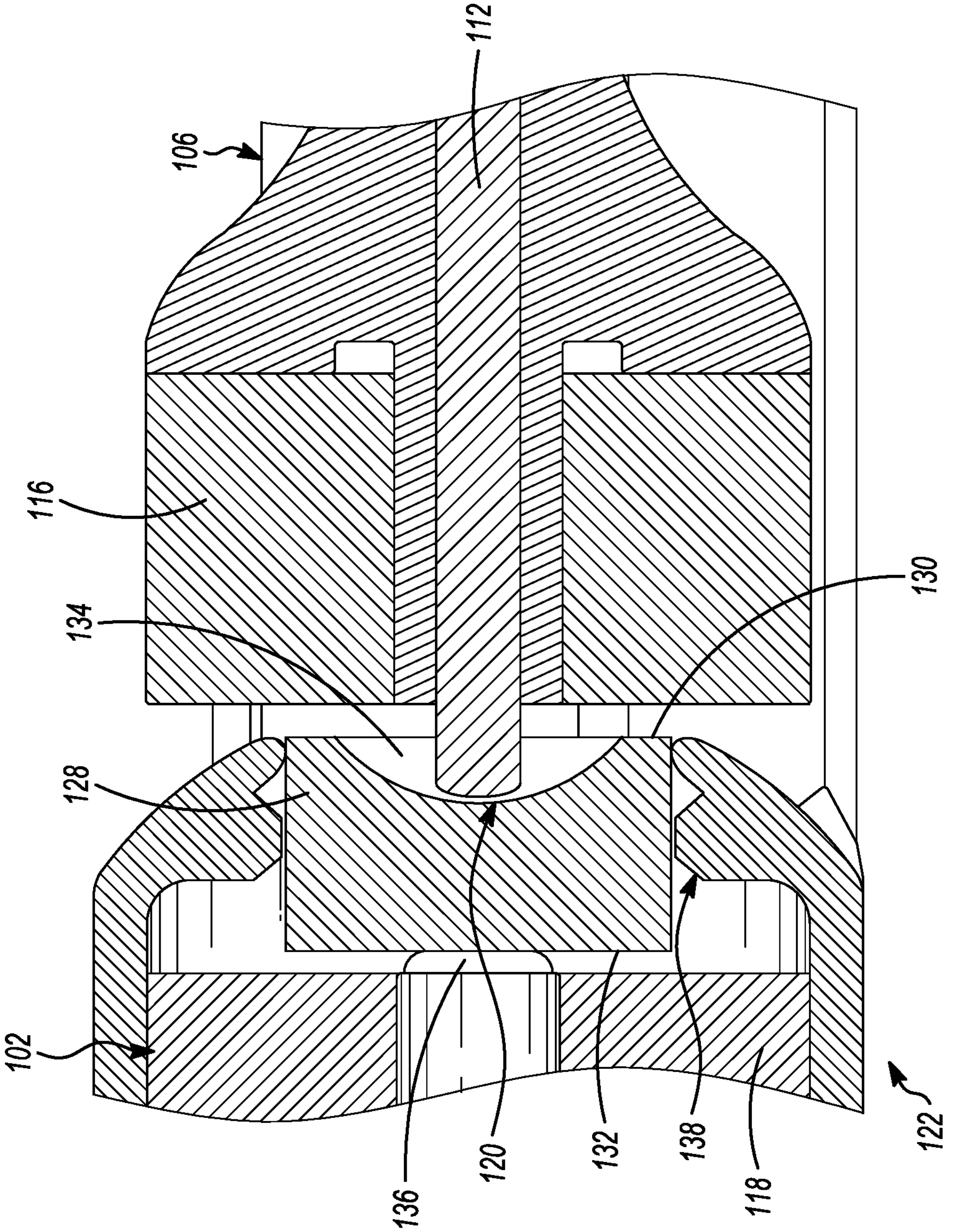
FIG. 1B is a close-up view of the first bearing assembly of FIG. 1A, in accordance with embodiments of the subject matter disclosed herein.

FIG. 1B is a close-up view of the first bearing assembly 122 of FIG. 1A, in accordance with embodiments of the subject matter disclosed herein. The second bearing assembly 126 may include, for example, a journal bearing, or any other type of suitable bearing. As shown in FIG. 1B, the first bearing assembly 122 includes a bearing 128 having a first side 130, facing toward the impeller assembly 106, and an opposite, second side 132, facing toward the motor 102. A concave depression 134 is defined in the first side 130 of the bearing 128. The concave depression 134 is configured to receive the first end 120 of the drive shaft 112. As shown, the first end 120 of the drive shaft 112 may be at least partially rounded and, in embodiments, may include a curvature corresponding to the curvature of the concave depression 134. In this manner, the surface area of contact between the drive shaft 112 and the bearing 128 may be as small as possible, reducing the chance that any blood cells will be able to get between the drive shaft 112 and the bearing 128 at their interface.

According to embodiments, the first bearing assembly 122 may also include a biasing feature 136 disposed between the second side 132 of the bearing 128 and the motor 102. The biasing feature 136 may have a compliance configured such that the biasing feature 136 biases the bearing 128 in the direction of the drive shaft 112, resisting the load generated by the attraction between the impeller rotor 116 and the stator 118, while allowing enough flexibility to prevent the bearing 128 from being cracked or otherwise broken by the load. The bearing 128 may also, as shown, be retained in place by a bearing support feature 138, which may be integrated into the motor housing 104, the impeller assembly housing 108, or which may be a separate feature coupled to the motor housing 104 and/or the impeller assembly housing 108. According to embodiments, the bearing support feature 138 may include any number of different types of features configured to maintain the bearing 128 in its position. For example, the bearing support feature 138 may include multiple edges, a notch configured to receive a tab or edge, edges configured to form an interference fit with the periphery of the bearing, and/or the like.

The illustrative circulatory support device 100 shown in FIGS. 1A and 1B is not intended to suggest any limitation as to the scope of use or functionality of embodiments of the present disclosure. The illustrative circulatory support device 100 also should not be interpreted as having any dependency or requirement related to any single component or combination of components illustrated therein. Additionally, various components depicted in FIGS. 1A and 1B may be, in embodiments, integrated with various ones of the other components depicted therein (and/or components not illustrated), all of which are considered to be within the ambit of the present disclosure.

Figure 2A:
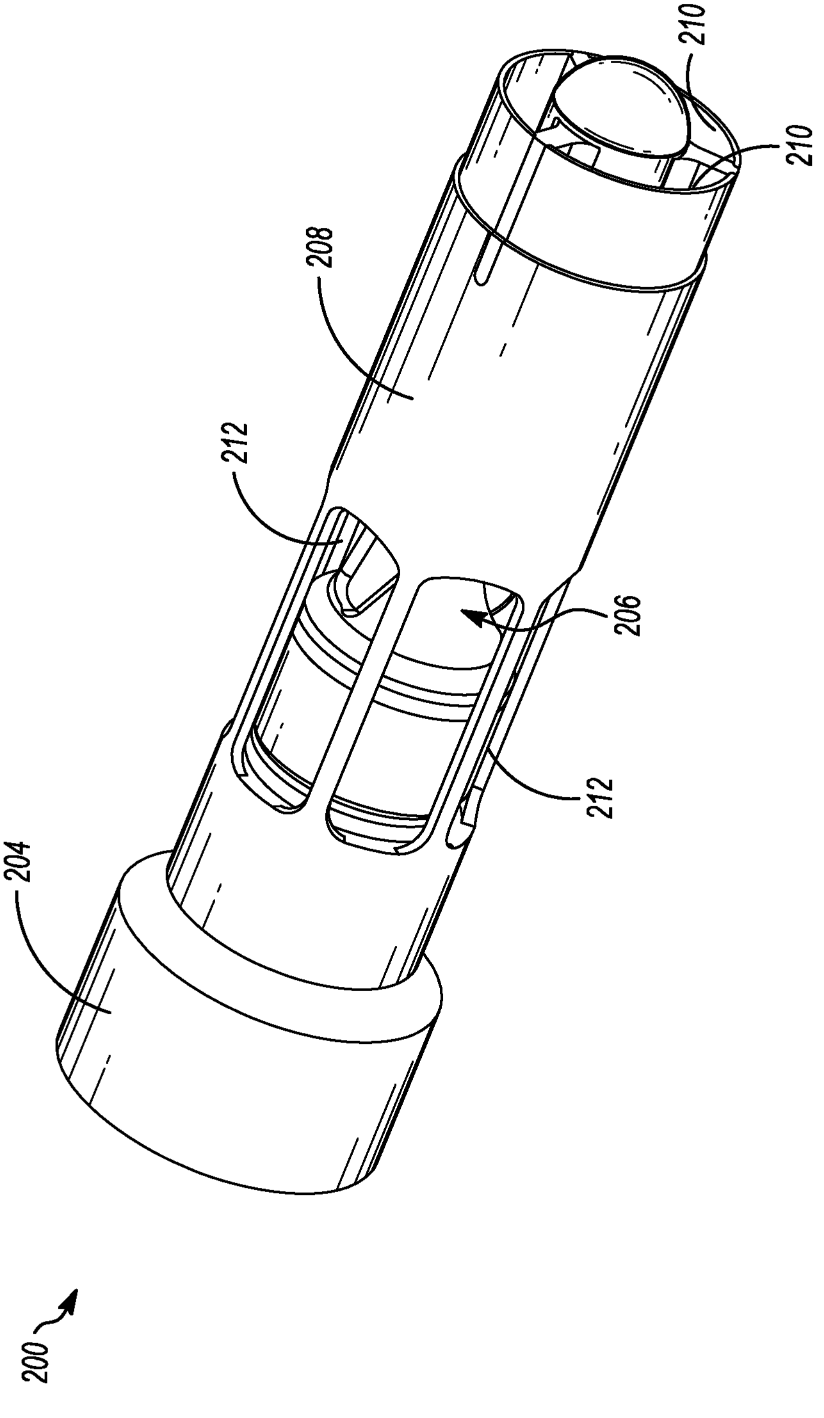
FIG. 2A depicts a perspective view of an illustrative percutaneous mechanical circulatory support device, in accordance with embodiments of the subject matter disclosed herein.
Figure 2B:
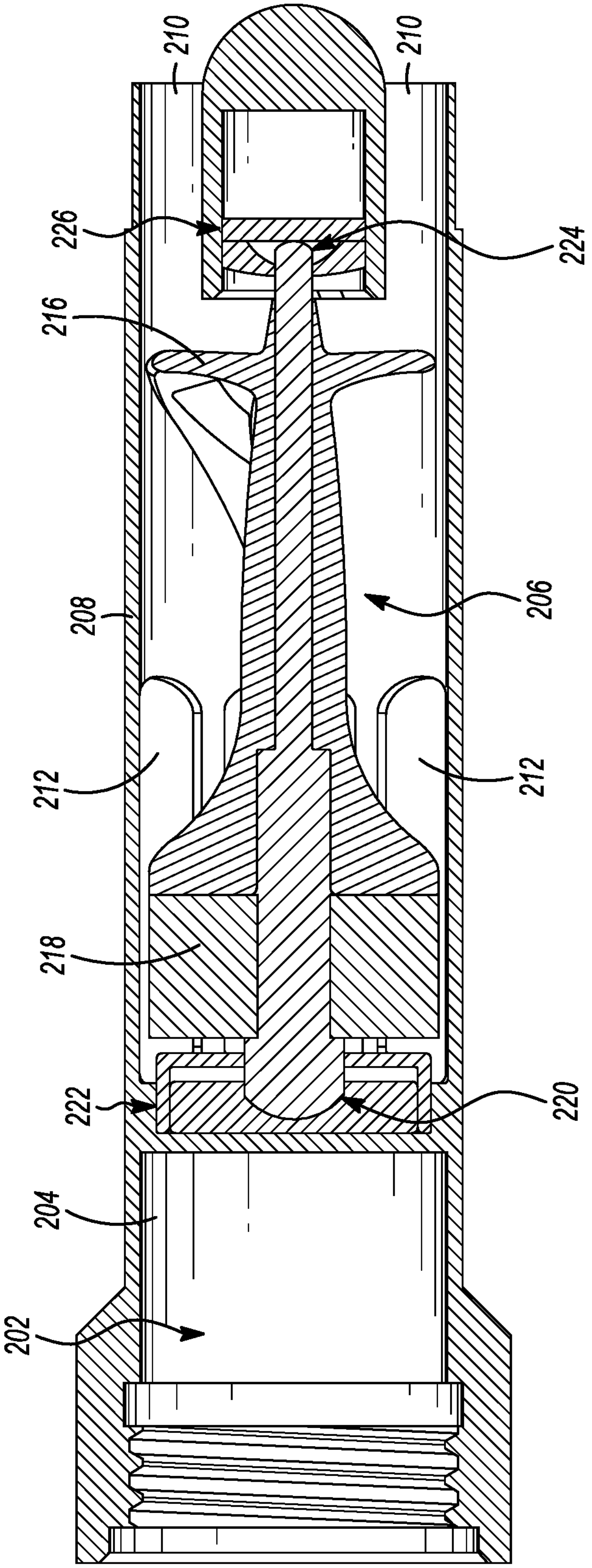
FIG. 2B depicts a cross-sectional side view of the circulatory support device depicted in FIG. 2A, in accordance with embodiments of the subject matter disclosed herein.

FIG. 2A depicts a perspective view of an illustrative percutaneous mechanical circulatory support device 200, in accordance with embodiments of the subject matter disclosed herein; and FIG. 2B depicts a cross-sectional side view of the circulatory support device 200 depicted in FIG. 2A, in accordance with embodiments of the subject matter disclosed herein. According to embodiments, the circulatory support device 200, and/or any number of various components thereof, may be the same as, or similar to, corresponding components of the circulatory support device 100 depicted in FIGS. 1A and 1B.

As shown in FIGS. 2A and 2B, the circulatory support device 200 includes a motor 202 disposed within a motor housing 204. The motor 202 is configured to drive an impeller assembly 206 to provide a flow of blood through the device 200. The impeller assembly 206 is disposed within an impeller assembly housing 208, which includes a number of inlet apertures 210 and a number of outlet apertures 112 defined therein. According to embodiments, the motor housing 204 and the impeller assembly housing 208 may be integrated with one another. In other embodiments, the motor housing 204 and the impeller assembly housing 208 may be separate components configured to be coupled together, either removeably or permanently. A controller (not shown) is operably coupled to the motor 202 and is configured to control the motor 202. The controller may be disposed within the motor housing 204 in embodiments, or, in other embodiments, may be disposed outside the housing 204 (e.g., in a catheter handle, independent housing, etc.). In embodiments, the controller may include multiple components, one or more of which may be disposed within the housing 204. According to embodiments, the motor 204 may be, be similar to, include, or be included in the motor 104 depicted in FIG. 1A.

As shown in FIG. 2B, the impeller assembly 206 includes a drive shaft 214 and an impeller 216 coupled thereto, where the drive shaft 214 is configured to rotate with the impeller 216. As shown, the drive shaft 214 is at least partially disposed within the impeller 216. In embodiments, the drive shaft 214 may be made of any number of different rigid materials such as, for example, steel, titanium alloys, cobalt chromium alloys, nitinol, high-strength ceramics, and/or the like. The impeller assembly 206 further includes an impeller rotor 218 coupled to, and at least partially surrounding, the drive shaft 214. The impeller rotor 218 may be any type of magnetic rotor capable of being driven by a stator (not shown, but which may be the same as, or similar to, the stator 118 depicted in FIGS. 1A and 1B) that is part of the motor 202. In this manner, as a magnetic field is applied to the impeller rotor 218 by the stator in the motor 202, the rotor 218 rotates, causing the drive shaft 214 and impeller 216 to rotate.

As shown, the impeller assembly is maintained in its orientation by the drive shaft 214, which is retained, at a first end 220, by a first bearing assembly 222 and, at a second end 224, by a second bearing assembly 226. According to embodiments, the first bearing assembly 222 and the second bearing assembly 226 may include different types of bearings. According to embodiments, the first bearing assembly 222 and/or the second bearing assembly 226 may include a lubricant chamber configured to hold a lubricant, while, in other embodiments, one and/or the other may not include lubrication. Various embodiments of bearing technology are described herein with respect to the first and second bearing assemblies 222 and 226.

Figure 2C:
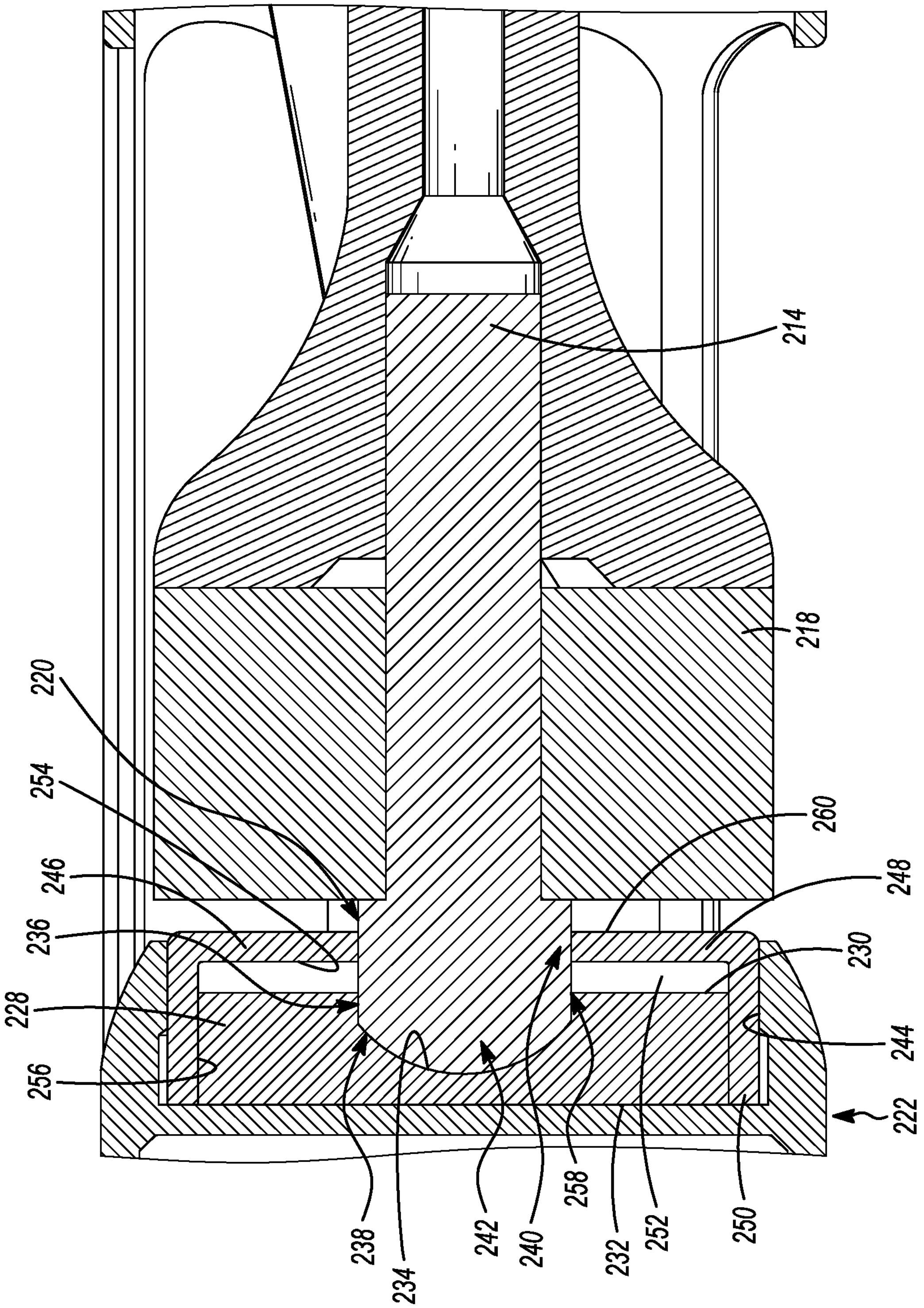
FIG. 2C is a close-up view of the first bearing assembly of FIG. 2B, in accordance with embodiments of the subject matter disclosed herein.

FIG. 2C is a close-up view of the first bearing assembly 222 of FIG. 2B, in accordance with embodiments of the subject matter disclosed herein. The second bearing assembly 226 may include, for example, a journal bearing, or any other type of suitable bearing. As shown in FIG. 2C, the first bearing assembly 222 includes a bearing 228 having a first side 230, facing toward the impeller assembly 206, and an opposite, second side 232, facing toward the motor 202. A concave depression 234 is defined in the first side 230 of the bearing 228. The concave depression 234 is configured to receive the first end 220 of the drive shaft 214. As shown, the first end 220 of the drive shaft 214 may be at least partially rounded and, in embodiments, the concave depression 234 may be sized to just fit the first end 22 of the drive shaft 214.

As shown in FIG. 2C, the concave depression 234 may include a first portion 236 and a second portion 238, where the first portion 236 has an at least approximately cylindrical shape and extends into the bearing 228 from the first side 230 of the bearing 228. The second portion 238 has an at least approximately concave shape. In embodiments, the first portion 236 may be sized to fit a corresponding first portion 240 of the first end 220 of the drive shaft 214, while the second portion 238 may be sized to fit a corresponding second portion 242 of the first end 220 of the drive shaft 214. In embodiments, the first portion 240 of the first end 220 of the drive shaft 214 may have an approximately cylindrical shape, and the second portion 242 of the first end 220 of the drive shaft 214 may have an approximately convex shape. In this manner, the first portion 238 of the depression 234 may facilitate maintaining the drive shaft 214 in its orientation.

Additionally, the concave geometry of the depression, in conjunction with the rounded end of the drive shaft, creates a relatively large bearing surface, thereby distributing axial load over more area. The diameter of the end of the drive shaft (and, thus, of the concave depression) may be configured to facilitate desired performance characteristics. For example, increasing these diameters may lead to higher velocity of rotation, while reducing axial stresses, thereby reducing friction. According to embodiments, the dimensions of the various aspects of the bearing assembly may be selected based on implementation, performance, materials, and/or the like.

According to embodiments, the first bearing assembly 222 may also include a biasing feature (not shown) disposed between the second side 232 of the bearing 228 and the motor 202. The biasing feature may have a compliance configured such that the biasing feature biases the bearing 228 in the direction of the drive shaft 214, resisting the load generated by the attraction between the impeller rotor 218 and the stator, while allowing enough flexibility to prevent the bearing 228 from being cracked or otherwise broken by the load. The bearing 228 may also, as shown, be retained in place by a bearing support feature 244, which may be integrated into the motor housing 204, the impeller assembly housing 208, or which may be a separate feature coupled to the motor housing 204 and/or the impeller assembly housing 208. According to embodiments, the bearing support feature 244 may include any number of different types of features configured to maintain the bearing 228 in its position. For example, the bearing support feature 244 may include multiple edges, a notch configured to receive a tab or edge, edges configured to form an interference fit with the periphery of the bearing, and/or the like.

As shown, the bearing assembly 222 may also include a cup washer 246 having a base 248 and a peripheral wall 250 extending away from the base 248 towards the motor 202, forming a cavity 252 bounded by an inner surface 254 of the base 248 and an inner surface 256 of the peripheral wall 250. The peripheral wall 250 may be oriented approximately orthogonal to the base 248. A shaft aperture 258 may be defined through the base 248, extending from an outer surface 260 of the base 248 to the inner surface 254 of the base 248, and may be configured to receive a portion of the drive shaft 214. As shown, the bearing 228 is configured to be at least partially disposed within the cavity 252.

Additionally, a lubricant may be disposed within the cavity to facilitate preservation of the bearing 228 and its interface with the drive shaft 214. That is, for example, at least a portion of a lubricant chamber may be defined between the inner surface 254 of the base 248 of the cup washer 246, the inner surface 256 of the peripheral wall 250 of the cup washer 246, and the first side 230 of the bearing 228. Additionally or alternatively, a portion of a lubricant chamber may be defined within the bearing (e.g., within the bearing 228). The lubricant may be any type of hydrophobic lubricant suitable for use in a blood pump. For example, in embodiments, but without intending to limit the disclosure, the lubricant may be a modified silicone lubricant such as, for example, a modified Polydimethylsiloxane (PDMS). In other embodiments, the lubricant may be an oil-based lubricant, a synthetic oil, a carbon-based lubricant, and/or the like.

The illustrative circulatory support device 200 shown in FIGS. 2A-2C is not intended to suggest any limitation as to the scope of use or functionality of embodiments of the present disclosure. The illustrative circulatory support device 200 also should not be interpreted as having any dependency or requirement related to any single component or combination of components illustrated therein. Additionally, various components depicted in FIGS. 2A-2C may be, in embodiments, integrated with various ones of the other components depicted therein (and/or components not illustrated), all of which are considered to be within the ambit of the present disclosure.

Figure 3:
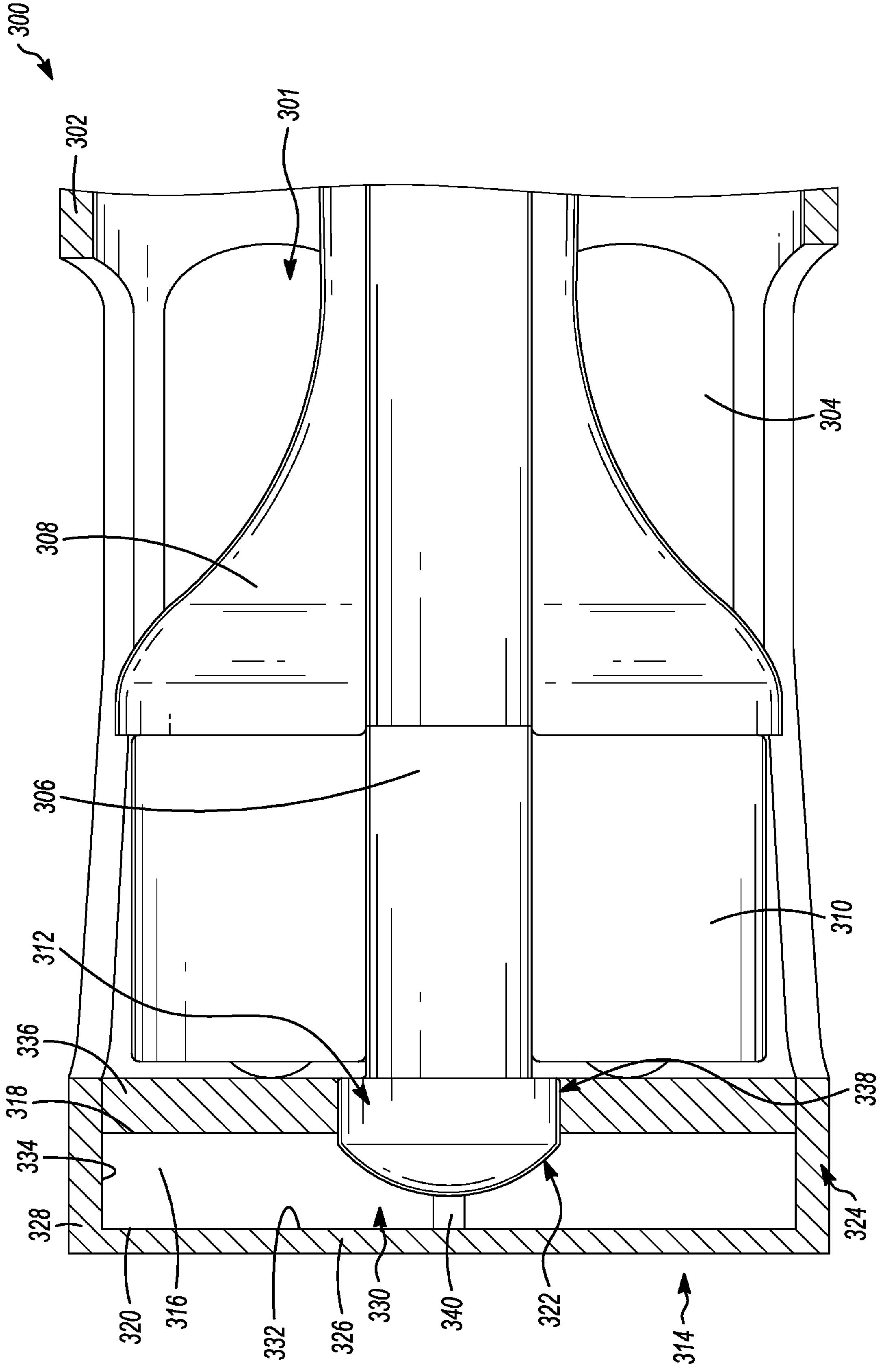
FIG. 3 depicts a cross-sectional side view of an illustrative circulatory support device having an impeller assembly, in accordance with embodiments of the subject matter disclosed herein.

FIG. 3 depicts a cross-sectional side view of an illustrative circulatory support device 300 having an impeller assembly 301, in accordance with embodiments of the subject matter disclosed herein. According to embodiments, the circulatory support device 300, and/or any number of various components thereof, may be the same as, or similar to, corresponding components of the circulatory support device 100 depicted in FIGS. 1A and 1B, and/or the circulatory support device 200 depicted in FIGS. 2A-2C.

As shown in FIG. 3, the impeller assembly 301 is disposed within an impeller assembly housing 302, which includes a number of outlet apertures 304 defined therein. The impeller assembly 301 includes a drive shaft 306 and an impeller 308 coupled thereto, where the drive shaft 306 is configured to rotate with the impeller 308. As shown, the drive shaft 306 is at least partially disposed within the impeller 308. In embodiments, the drive shaft 306 may be made of any number of different rigid materials such as, for example, steel, titanium alloys, cobalt chromium alloys, nitinol, high-strength ceramics, and/or the like. The impeller assembly 308 further includes an impeller rotor 310 coupled to, and at least partially surrounding, the drive shaft 306. The impeller rotor 310 may be any type of magnetic rotor capable of being driven by a stator (not shown, but which may be the same as, or similar to, the stator 118 depicted in FIGS. 1A and 1B) that is part of the motor. In this manner, as a magnetic field is applied to the impeller rotor 310 by the stator in the motor, the rotor 310 rotates, causing the drive shaft 306 and impeller 308 to rotate.

As shown, the impeller assembly 301 is maintained in its orientation by the drive shaft 306, which is retained, at a first end 312, by a first bearing assembly 314 and, at a second end (not shown), by a second bearing assembly (not shown). According to embodiments, the first bearing assembly 314 and the second bearing assembly may include different types of bearings. According to embodiments, the first bearing assembly 314 and/or the second bearing assembly may include a lubricant chamber configured to hold a lubricant. The first bearing assembly 314 includes a bearing 316 having a first side 318, facing toward the impeller assembly 301, and an opposite, second side 320, facing toward the motor. A concave depression 322 is defined in the first side 318 of the bearing 316. The concave depression 322 is configured to receive the first end 312 of the drive shaft 306 and may, in embodiments, be configured in a manner similar to the concave depression 134 depicted in FIG. 1B and/or the concave depression 234 depicted in FIG. 2C. As shown, the first end 312 of the drive shaft 214 may configured similar to the first end 120 of the drive shaft 112 depicted in FIGS. 1A and 1B and/or the first end 220 of the drive shaft 214 depicted in FIGS. 2B-2C. According to embodiments, the first bearing assembly 314 may also include a biasing feature (not shown) disposed between the second side 320 of the bearing 316 and the motor.

As shown, the bearing assembly 314 may also include a cup washer 324 or other similar basin-like structure, having a base 326 and a peripheral wall 328 extending away from the base 326 toward the impeller assembly 301, forming a cavity 330 bounded by an inner surface 332 of the base 326 and an inner surface 334 of the peripheral wall 328. As shown, the bearing 316 is configured to be at least partially disposed within the cavity 330. A cover 336 may be disposed adjacent to the first side 318 of the bearing 316, and include a shaft aperture 338 configured to receive a portion of the drive shaft 306. In embodiments, for example, the cover 336 may be a layer of graphite, a polymer, and/or the like.

As is further shown in FIG. 3, the bearing assembly 314 includes a lubricant chamber configured to retain a lubricant. The lubricant chamber may include at least one channel 340 defined in the second side 320 of the bearing 316. In embodiments, the channel or channels pass through the depression 322. According to embodiments, the bearing 316 may include two or more channels 340 defined therein. As can be seen from FIG. 3, at least a portion of the inner surface 332 of the base 326 may form a boundary of the lubricant chamber.

The illustrative circulatory support device 300 shown in FIG. 3 is not intended to suggest any limitation as to the scope of use or functionality of embodiments of the present disclosure. The illustrative circulatory support device 300 also should not be interpreted as having any dependency or requirement related to any single component or combination of components illustrated therein. Additionally, various components depicted in FIG. 3 may be, in embodiments, integrated with various ones of the other components depicted therein (and/or components not illustrated), all of which are considered to be within the ambit of the present disclosure.

Figure 4:
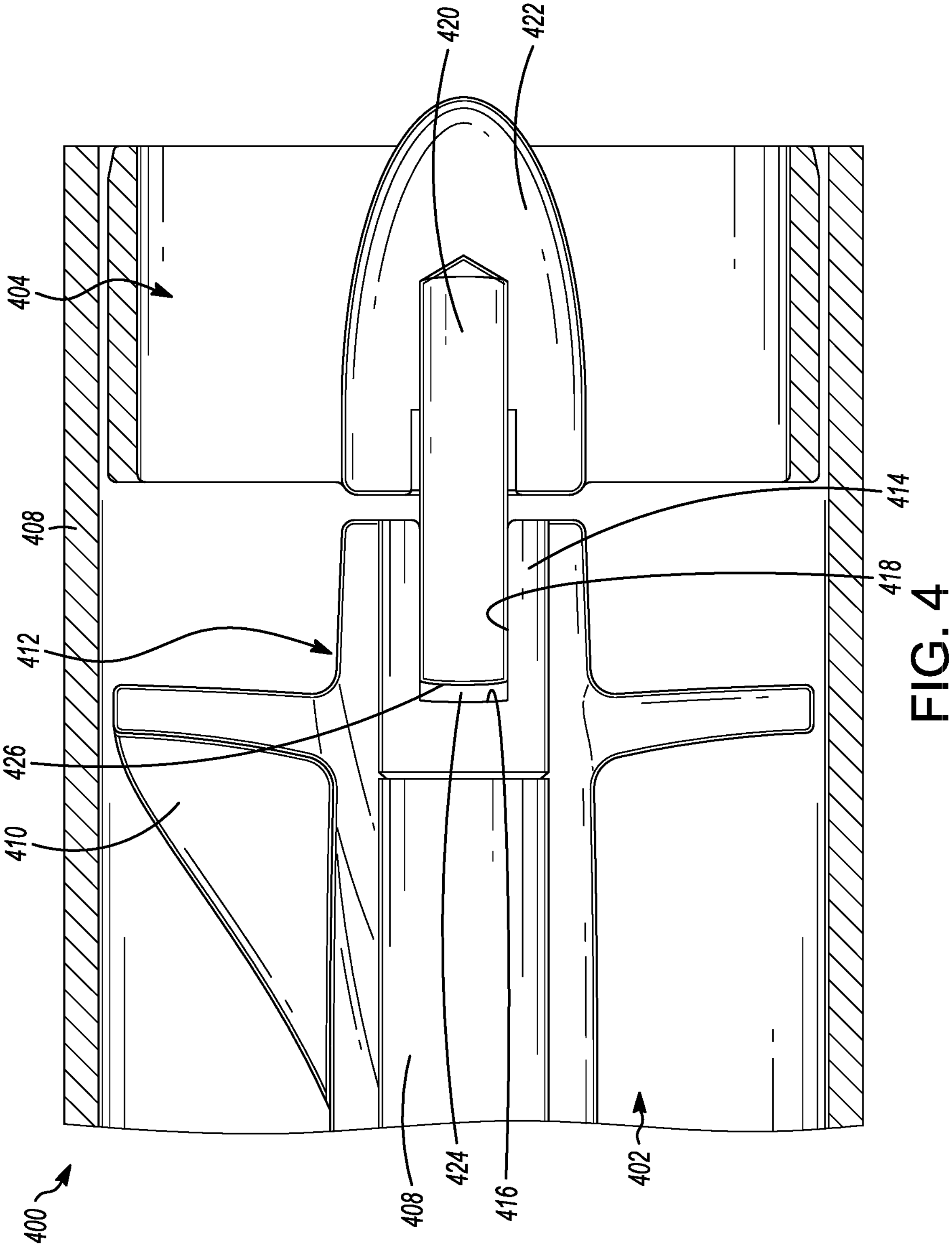
FIG. 4 depicts a cross-sectional side view of an illustrative circulatory support device having an impeller assembly, in accordance with embodiments of the subject matter disclosed herein.

FIG. 4 depicts a cross-sectional side view of an illustrative circulatory support device 400 having an impeller assembly 402, in accordance with embodiments of the subject matter disclosed herein. According to embodiments, the circulatory support device 400, and/or any number of various components thereof, may be the same as, or similar to, corresponding components of the circulatory support device 100 depicted in FIGS. 1A and 1B, the circulatory support device 200 depicted in FIGS. 2A-2C, and/or the circulatory support device 300 depicted in FIG. 3. In embodiments, the portion of the circulatory support device 400 depicted in FIG. 4 is the portion of an impeller assembly associated with an end opposite the end adjacent the motor. That is, for example, the bearing assembly 404 depicted in FIG. 4 may be, be similar to, and/or otherwise correspond to the bearing assembly 126 depicted in FIG. 1A and/or the bearing assembly 226 depicted in FIG. 2B. In embodiments, implementations of the bearing assembly 404 may be used, alternatively or additionally, as the bearing assembly 122 depicted in FIGS. 1A and 1B, the bearing assembly 222 depicted in FIGS. 2B and 2C, the bearing assembly 314 depicted in FIG. 3, and/or the like.

As shown in FIG. 4, the impeller assembly 402 is disposed within an impeller assembly housing 406, which includes a number of apertures (not shown) defined therein. The impeller assembly 402 includes a drive shaft 408 and an impeller 410 coupled thereto, where the drive shaft 408 is configured to rotate with the impeller 410. As shown, the drive shaft 408 is at least partially disposed within the impeller 410. In embodiments, the drive shaft 408 may be made of any number of different rigid materials such as, for example, steel, titanium alloys, cobalt chromium alloys, nitinol, high-strength ceramics, and/or the like.

The impeller assembly 402 is maintained in its orientation by the drive shaft 408, which is retained, at a first end (not shown), by a first bearing assembly (not shown) and, at a second end 412, by the bearing assembly. According to embodiments, the first bearing assembly and the second bearing assembly 404 may include different types of bearings. According to embodiments, the first bearing assembly and/or the second bearing assembly 404 may include a lubricant chamber configured to hold a lubricant. The bearing assembly 404 includes a cylindrical-shaped bearing 414 disposed in the end 412 of the drive shaft 408. The bearing 414 includes a first inside surface 416 facing away from the impeller and a second inside surface 418 extending away from the first inside surface. According to embodiments, the second inside surface 418 may be oriented approximately orthogonal to the first inside surface 416.

As shown in FIG. 4, cylindrical-shaped bearing is disposed at an intersection of the drive shaft 408 and a stationary shaft mounting pin 420. The shaft mounting pin may be made of any number of different materials. For example, in some embodiments, the shaft mounting pin 420 may be made of the same material as the drive shaft 408. The shaft mounting pin 420 may be coupled to a pin support 422. The drive shaft 408 is configured to rotate with respect to the stationary shaft mounting pin 420. To facilitate reduction of friction and preservation of the bearing assembly 404, the bearing assembly 404 may include a lubricant chamber 424. The lubricant chamber 424 may be defined between the first inner surface 416 of the bearing 414 and an outer surface 426 of the stationary shaft mounting pin 420. The lubricant chamber 424 may be further bounded by at least a portion of the second inner surface 418 of the bearing 414.

The illustrative circulatory support device 400 shown in FIG. 4 is not intended to suggest any limitation as to the scope of use or functionality of embodiments of the present disclosure. The illustrative circulatory support device 400 also should not be interpreted as having any dependency or requirement related to any single component or combination of components illustrated therein. Additionally, various components depicted in FIG. 4 may be, in embodiments, integrated with various ones of the other components depicted therein (and/or components not illustrated), all of which are considered to be within the ambit of the present disclosure.

Figure 5A:
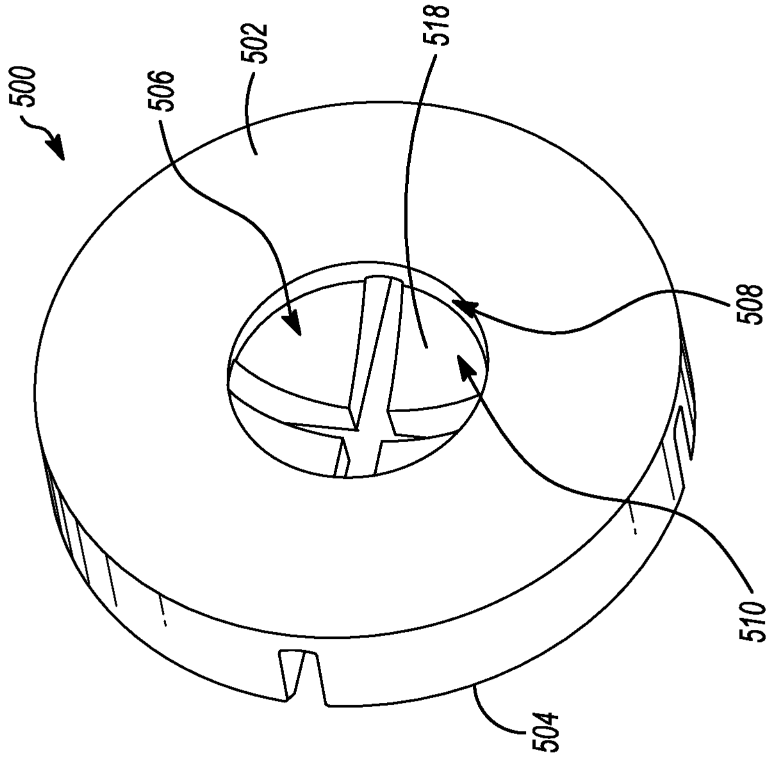
FIGS. 5A and 5B are perspective views of an illustrative bearing, in accordance with embodiments of the subject matter disclosed herein.
Figure 5B:
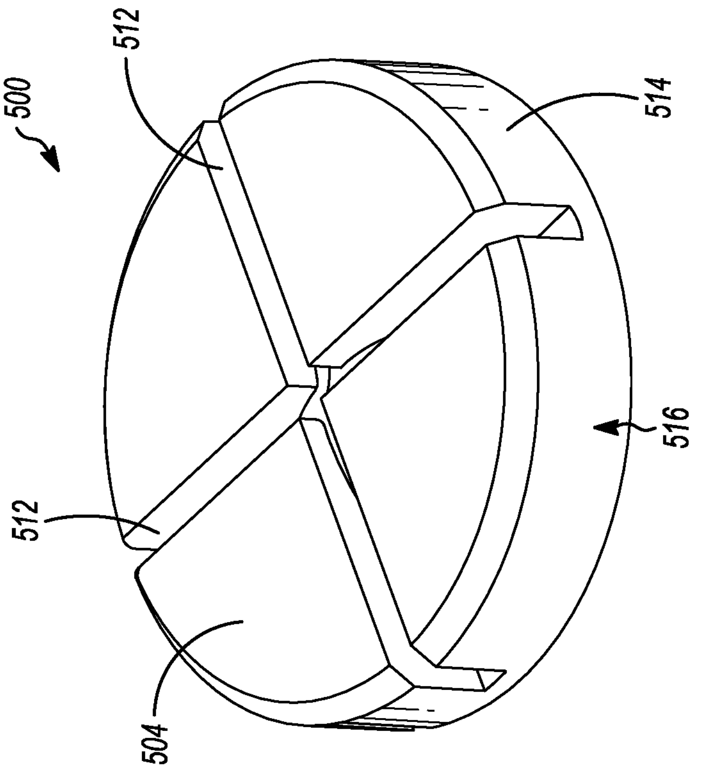

As indicated above, a portion of a lubricant chamber may be defined within a bearing. FIGS. 5A and 5B are perspective views of an illustrative bearing 500, in accordance with embodiments of the subject matter disclosed herein. According to embodiments, the bearing 500 may be, or be similar to, the bearing 122 depicted in FIGS. 1A and 1B, the bearing 222 depicted in FIGS. 2A-2C, the bearing 322 depicted in FIG. 3, and/or the like. In embodiments, the bearing 500 includes a first side 502, configured to face toward an impeller assembly, and an opposite, second side 504, configured to face toward a motor. A concave depression 506 is defined in the first side 502 of the bearing 500. The concave depression 506 is configured to receive an end of a drive shaft. As discussed herein, the end of the drive shaft may be at least partially rounded and, in embodiments, the concave depression 506 may be sized to just fit the end of the drive shaft.

As shown, the concave depression 500 may include a first portion 508 and a second portion 510, where the first portion 508 has an at least approximately cylindrical shape and extends into the bearing 500 from the first side 502 of the bearing 500. The second portion 510 has an at least approximately concave shape. In embodiments, the first portion 508 may be sized to fit a corresponding first portion of the end of the drive shaft, while the second portion 510 may be sized to fit a corresponding second portion of the end of the drive shaft. In embodiments, the first portion of the end of the drive shaft may have an approximately cylindrical shape, and the second portion of the end of the drive shaft may have an approximately convex shape. In this manner, the first portion 508 of the depression 506 may facilitate maintaining the drive shaft in its orientation.

As is further shown, two channels 512 are defined in the second side 504 of the bearing 500. According to embodiments, the bearing 500 may include any number of channels (e.g., 1, 2, 3, 4, 5, etc.) having any number of different depths, widths, and/or the like. In embodiments, for example, the channels do not extend through the outside surface 514 of the periphery wall 516. In embodiments, the bearing 500 may include multiple channels of varying size. For example, the bearing 500 may include microchannels (e.g., channels that are substantially narrower and shallower than the channels 512 such as, for example, by at least a factor of 5) defined in an upper surface 518 of the concave depression. According to embodiments, using bearings with channels defined therein for lubricant chambers may facilitate using thinner bearings, thereby enabling the rotor of the impeller assembly to be closer to the stator of the motor, which may enable increased torque and efficiency.

The bearing 500 shown in FIGS. 5A and 5B is not intended to suggest any limitation as to the scope of use or functionality of embodiments of the present disclosure. The illustrative bearing 500 also should not be interpreted as having any dependency or requirement related to any single component or combination of components illustrated therein. Additionally, various components depicted in FIGS. 5A and 5B may be, in embodiments, integrated with various ones of the other components depicted therein (and/or components not illustrated), all of which are considered to be within the ambit of the present disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A blood pump, comprising:

an impeller;

a drive shaft coupled to the impeller and configured to rotate with the impeller, a proximal end region of the drive shaft extending proximal of the impeller;

a motor configured to drive the impeller; and a proximal bearing assembly disposed proximal of the impeller and configured to receive a proximal end of the drive shaft, the bearing assembly comprising a proximal bearing, wherein the proximal end of the drive shaft has a convex surface, and wherein the proximal bearing includes a concave depression having a concave surface, wherein the concave depression is configured to receive the proximal end of the drive shaft such that the concave surface contacts the convex surface;

wherein the proximal bearing includes at least one channel formed in the concave depression and extending proximally from the concave surface, the at least one channel opening out to the concave surface and extending radially outward to an outer peripheral surface of the proximal bearing; and wherein the convex surface of the proximal end of the drive shaft extends across the at least one channel.

2. The blood pump of claim 1, wherein the at least one channel includes a plurality of channels.

3. The blood pump of claim 1, further comprising a driven magnet surrounding the proximal end region of the drive shaft.

4. The blood pump of claim 3, wherein the driven magnet is positioned between a proximal end of the impeller and the proximal end of the drive shaft.

5. The blood pump of claim 1, wherein a distal end of the drive shaft is positioned proximal of a distal end of the impeller.

6. The blood pump of claim 5, further comprising a distal bearing assembly disposed distal of the impeller.

7. The blood pump of claim 6, wherein the distal bearing assembly includes a distal bearing disposed within a lumen of the impeller.

8. The blood pump of claim 7, wherein the distal end of the drive shaft is located proximal of the distal bearing.

9. The blood pump of claim 7, wherein the distal bearing assembly includes a stationary shaft mounting pin extending into the lumen of the impeller.

10. The blood pump of claim 9, wherein the distal bearing surrounds the stationary shaft mounting pin.

11. The blood pump of claim 10, wherein the impeller is configured to rotate relative to the stationary shaft mounting pin.

12. A blood pump, comprising:

an impeller housing;

an impeller disposed within the impeller housing;

a drive shaft having a distal end region extending into a lumen of the impeller and a proximal end region extending proximal of the impeller, wherein the impeller is configured to rotate with the drive shaft relative to the impeller housing;

a motor configured to rotate the drive shaft to drive the impeller;

a proximal bearing assembly disposed proximal of the impeller;

a distal bearing assembly disposed distal of the impeller;

wherein the proximal bearing assembly and the distal bearing assembly support the impeller within the impeller housing;

wherein the proximal bearing assembly includes a proximal bearing having a distally facing concave depression defining a concave surface, wherein a proximal end of the drive shaft has a convex surface contacting the concave surface of the concave depression;

wherein the proximal bearing includes at least one channel formed in the concave depression and extending proximally from the concave surface, the at least one channel opening out to the concave surface and extending radially outward to an outer peripheral surface of the proximal bearing; and wherein the convex surface of the proximal end of the drive shaft extends across the at least one channel.

13. The blood pump of claim 12, wherein the distal bearing assembly includes a distal bearing disposed within the lumen of the impeller.

14. The blood pump of claim 13, wherein a distal end of the drive shaft is located proximal of the distal bearing.

15. The blood pump of claim 14, wherein the distal bearing assembly includes a stationary shaft mounting pin extending into the lumen of the impeller.

16. The blood pump of claim 15, wherein the distal bearing surrounds the stationary shaft mounting pin.

17. The blood pump of claim 16, wherein the impeller is configured to rotate relative to the stationary shaft mounting pin.

18. The blood pump of claim 12, further comprising a driven magnet surrounding the proximal end region of the drive shaft.

19. The blood pump of claim 18, wherein the driven magnet is positioned between a proximal end of the impeller and the proximal end of the drive shaft.

20. The blood pump of claim 12, wherein a distal end of the drive shaft is positioned proximal of a distal end of the impeller.

* * * * *